United States Patent
Voelkel et al.

(10) Patent No.: US 6,815,469 B1
(45) Date of Patent: Nov. 9, 2004

(54) BIODEGRADABLE, INJECTABLE OLIGOMER-POLYMER COMPOSITION

(75) Inventors: Christoph Voelkel, Jena (DE); Manuela Pfeiffer, Jena (DE); Sabine Fricke, Jena (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/913,555

(22) PCT Filed: Feb. 11, 2000

(86) PCT No.: PCT/DE00/00444
§ 371 (c)(1),
(2), (4) Date: Jan. 16, 2002

(87) PCT Pub. No.: WO00/48643
PCT Pub. Date: Aug. 24, 2000

(30) Foreign Application Priority Data

Feb. 20, 1999 (DE) .......................... 199 08 753

(51) Int. Cl.⁷ .............................. C08K 5/10; C08K 5/11
(52) U.S. Cl. .................... 523/105; 523/113; 523/124; 524/314; 524/315; 524/317
(58) Field of Search ................. 523/105, 113, 523/124; 524/314, 315, 317

(56) References Cited

U.S. PATENT DOCUMENTS

| | | |
|---|---|---|
| 4,938,763 A | 7/1990 | Dunn et al. |
| 5,278,201 A | 1/1994 | Dunn et al. |
| 5,278,202 A | 1/1994 | Dunn et al. |
| 5,702,717 A | 12/1997 | Cha et al. |
| 5,783,205 A * | 7/1998 | Berggren et al. ........... 424/426 |

FOREIGN PATENT DOCUMENTS

| | | |
|---|---|---|
| EP | 0 275 961 A | 7/1988 |
| EP | 0 544 097 A | 6/1993 |

* cited by examiner

Primary Examiner—Kriellion A. Sanders
(74) Attorney, Agent, or Firm—Michael J. Striker

(57) ABSTRACT

A biodegradable, injectable oligomer-polymer composition is described, which consists of a combination of at least two biologically degradable inert materials and at least one biologically active ingredient. The inventive, oligomer-polymer composition coagulates when injected into the body of a mammal and forms an implant, from which the biologically active ingredient is released. The rate of release can be adjusted by controlling the type and amount of the ingredients of the oligomer-polymer composition.

14 Claims, 2 Drawing Sheets

BIODEGRADABLE, INJECTABLE OLIGOMER-POLYMER COMPOSITION

BACKGROUND OF THE INVENTION

1. Field of the Invention

In the present invention relates to a biodegradable, injectable oligomer-polymer composition consisting of a combination of at least two biologically degradable inactive materials and at least one biologically active ingredient.

2. Description of the Related Art

Implants for applying biologically active materials can be produced by compacting under aseptic conditions. These implants have the disadvantage that they are incapable of adapting to the spatial conditions of the site of the application and cause a sensation of pressure or pain there after the application.

A known solution to the problem of producing injectable implants furthermore consists of the use of microcapsules. The most common methods for producing microcapsules or microspheres are the so-called solvent evaporation technique, the spray-drying technique or the double emulsion technique. These methods require organic solvents or solvent mixtures such as dichloromethane, trichloromethane or a mixture of dichloromethane and methanol, which are toxic or at least physiologically hazardous for the living organism. The residual solvent content is therefore a common disadvantage of these methods. Moreover, the spray-drying method is associated with a relatively high expenditure for equipment.

Furthermore, the possibility exists of producing an implant in situ, when a solution or suspension of the biologically active material is applied parenterally. The in situ formation of an implant can be induced in various ways. In the U.S. Pat. No. 4,938,763, the biologically active substance is dissolved or dispersed in a solution of the biodegradable polymer, such as a polylactide, and this solution or dispersion is injected. After the injection, a solid implant, consisting of the precipitated or coagulated biodegradable polymer and the biologically active substance, is formed on contact with the body fluid. The solvent migrates out of the implant and is distributed in the organism. It is a disadvantage of this method, that the solvents used, such as N-methyl-2-pyrrolidone, are physiologically active and therefore can be applied parenterally only to a slight extent, if at all.

Furthermore, in the patents cited, as well as in other patents (U.S. Pat. Nos. 5,278,201 and 5,278,202), liquid acrylate-terminated prepolymers, which can be synthesized, for example, by reacting poly(D,L-lactide-co-ε-caprolactone) with reactive acrylic acid derivatives, are proposed as in situ implant materials. The liquid prepolymer is injected in admixture with the biologically active substance and a suitable initiator, such as (dibenzoyl peroxide), which initiates the curing of the prepolymer and, with that, the formation of the implant in the body. The considerably higher synthesis and purification expenses for preparing the biologically degradable polymers and the parenteral administration of a physiologically hazardous, free radical-forming substance as initiator are disadvantages of this method. In addition, there has been no prior experience with the biocompatibility of said acrylate-terminated prepolymers or with the biodegradable of the implant formed form these substances.

In the U.S. Pat. No. 5,702,717, the block copolymers of polyethylene glycol and polylactide or polycaprolactone are described, which, in aqueous solution at room temperature, are in the form of an injectable liquid and, at body temperature, form a gel, which contains the biologically active material. It is a disadvantage of this variation that the temperature for the transition from sol to gel depends on a plurality of different parameters, such as the composition and the degree of polymerization of the individual blocks in the block copolymer, the molecular weight of the block copolymer as well as the polymer concentration in the aqueous solution.

SUMMARY OF THE INVENTION

It is an object of the present invention to make available an oligomer-polymer composition as injectable implant, which overcomes the disadvantages of the state of the art.

Pursuant to the invention, this objective is accomplished owing to the fact that an oligomer-polymer composition, consisting of a combination of at least two biologically degradable inert materials and at least one biologically active ingredient is made available.

Pursuant to the invention, the biologically degradable inert materials preferably are polymerization products of identical or different hydroxycarboxylic acids.

Lactic acid or glycolic acid are particularly preferred as hydroxycarboxylic acids.

It is furthermore preferred pursuant to the invention that in each case at least one of the biologically degradable inert materials is a liquid low molecular weight oligomer and the other a solid, higher molecular weight polymer.

Furthermore, it is preferred, pursuant to the invention, that the liquid, low molecular weight oligomer is a compound of the general Formula I, II or III

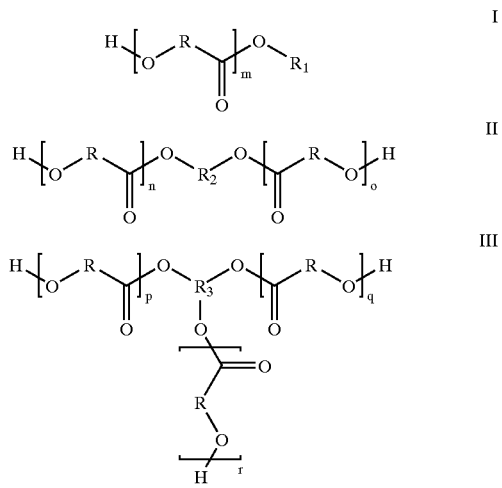

wherein
R is the same or different for the variables m, n, o, p, q and r and represents —$CH_2$—, —$CH(CH_3)$—, —$(CH_2)_5$—, —$CH_2$—$CH_2$—O—$CH_2$—, —$CH_2$—$CH_2$—O—$CH_2$—$CH_2$—O—$CH_2$— or their homologues with up to 5 further C atoms in each case;
$R_1$ represents —$CH_2$—COOY, —$CH(CH_3)$—COOY, —$CH_2$—$CH_2$—COOY, —$CH_2$—$CH_2$—$CH_2$—COOY, —$CH_2$—$CH_2$—$CH_2$—$CH_2$—COOY, —$CH_2$—$CH_2$—$CH_2$—$CH_2$—$CH_2$—COOY, —$CH_2$—$CH(CH_3)$—Y, —(cyclo-$C_6H_{11}$) or —$CH_2$—$C_6H_5$—;
$R_2$ represents —$CH_2$—$CH(CH_3)$—, —$CH_2$—$CH_2$—$CH_2$—, —$CH_2$—$CH_2$—$CH_2$—$CH_2$—, —$CH_2$—$CH_2$—

CH$_2$—CH$_2$—CH$_2$—, —(CH$_2$)$_2$—O—(CH$_2$)$_2$—O—(CH$_2$)$_2$—, —(CH$_2$)$_2$—O—(CH$_2$)$_2$—O—(CH$_2$)$_2$—O—(CH$_2$)$_2$—, —(CH$_2$)$_2$—O—(CH$_2$)$_2$—O—(CH$_2$)$_2$—O—(CH$_2$)$_2$—O—(CH$_2$)$_2$—, —CH$_2$—CH(—Y)—CH$_2$—, cyclohexane-1,2-diyl cyclohexane-1,3-diyl or cyclohexane-1,4-diyl;

R$_3$ represents (—CH$_2$)$_2$CH—, (—CH$_2$)$_3$C—CH$_3$ or (—CH$_2$)$_3$C—CH$_2$—CH$_3$, Y is —H, —CH$_3$, —C$_2$H$_5$, —C$_3$H$_7$ or —C$_4$H$_9$, and m, n, o, p, q and r denote, independently of one another, an integer from 2 to 18.

m, n, o, p, q and r independently of one another being a whole number from 2 to 18.

It is especially preferred if R is —CH(CH$_3$)—, R$_1$ is —CH(CH$_3$)—COOY, Y is —C$_2$H$_5$ and m, n, o, p, q or r is a whole number from 2 to 4.

Therefore, for the synthesis of the implants, preferably poly(hydroxyesters), such as poly-(L-lactides), poly-(D,L-lactides), polyglycolides, poly-(caprolactones), poly(dioxanones), poly-(hydroxybutyric acids), poly-(hydroxyvaleric acids, poly-(glycosalicylates) and copolymers of these compounds are used. In particular, poly-(hydroxy esters), which are synthesized by a ring-opening polymerization of lactones in the presence of a biocompatible starter molecule, are preferred. Suitable lactones for carrying out the ring-opening polymerization preferably are, for example, L-lactide, D,L-lactide, glycolide, p-dioxanone and e-caprolactone. Suitable biocompatible starter molecules are preferably aliphatic or cycloaliphatic compounds, which contain one or more free hydroxyl groups. Particularly suitable starter molecules are, for example, alkyl esters of L-lactic acid, cholesterol, 1,2-dihydroxypropane, triethylene glycol, glycerol or pentaerythritol.

It is furthermore preferred that the ratio of solid higher molecular weight polymers to the liquid lower molecular weight oligomers is 1:100 to 1:1 and especially 1:10 to 1:2.

The inventive, pharmaceutical composition is furthermore characterized in that the biologically active ingredient is selected from the group comprising the hormones, immune modulators, immune suppressive agents, antibiotics, cytostatic agents, diuretics, gastrointestinal drugs, cardiovascular drugs, and neuropharmacological drugs.

Pursuant to the invention, the biologically active ingredient preferably is present in dissolved or suspended form in the combination of inert materials.

Pursuant to the invention, the pharmaceutical composition is in the form of an injectable agent which, after the injection, can form a coagulate under the influence of the body fluid.

Furthermore, an object of the present invention is an injectable implant, which is obtainable by injecting an inventive, pharmaceutical composition into a body.

A further object of the invention is a method for the preparation of an injectable implant, wherein an inventive pharmaceutical composition is injected into the body of a mammal.

In other words, the object is accomplished pursuant to the invention owing to the fact that an in situ implant, which can be produced by placing a sterile, injectable composition of a biodegradable polymer, a biodegradable oligomer and the biologically active material in the organism and coagulating it under the influence of the body fluid, is made available.

The present invention accordingly relates to biologically degradable compositions of oligomeric and polymeric esters of hydroxycarboxylic acids, which can be produced by selecting suitable oligomeric and polymeric components as homogeneous solutions of adjustable viscosity or solids of low melting point without the use of further solvents or plasticizers. Said compositions of oligomers and polymers, after being injected into the human or animal organism, are capable of forming in situ coagulates under the influence of body fluid. The in situ implants, formed in this matter, can be used for the administration of biologically active materials in the organism.

During an investigation of a large number of biocompatible solvents or complexing agents, it was surprisingly found that biodegradable polymers, especially those of the group of polyhydroxy esters and their copolymers can be dissolved or converted into soluble complexes by oligomers of different hydroxycarboxylic acids with defined structures in a wide range of concentrations. These solutions or soluble complexes can be administered parenterally in a sterile form and, under the influence of body fluid, form coagulates in situ.

Furthermore, implants are preferred in which the biodegradable oligomer is a compound of the general Formula I, II, or III

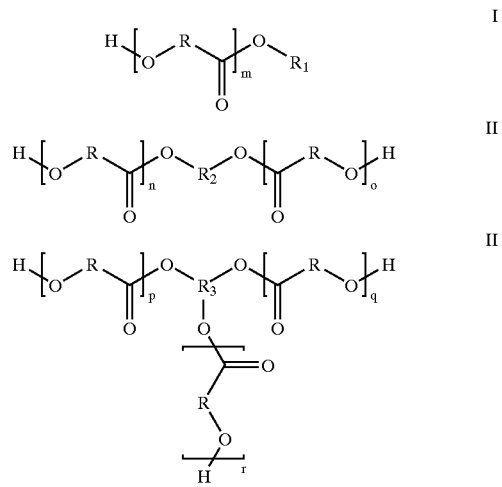

wherein

R is the same or different for the variables m, n, o, p, q and r represents —CH$_2$—, —CH(CH$_3$)—, —(CH$_2$)$_5$—, —CH$_2$—CH$_2$—O—CH$_2$—, —CH$_2$—CH$_2$—O—CH$_2$—CH$_2$—O—CH$_2$— or their homologs with in each case up to 5 further carbon atoms;

R$_1$ represents —CH$_2$—COOY, —CH(CH$_3$)—COOY, —CH$_2$—CH$_2$—COOY, —CH$_2$—CH$_2$—CH$_2$—COOY, —CH$_2$—CH$_2$—CH$_2$—CH$_2$—COOY, —CH$_2$—CH$_2$—CH$_2$—CH$_2$—CH$_2$—COOY, —CH$_2$—CH(CH$_3$)—Y, —(cyclo-C$_6$H$_{11}$) or —CH$_2$—C$_6$H$_5$, R$_2$ represents —CH$_2$—CH(CH$_3$)—, —CH$_2$—CH$_2$—CH$_2$—, —CH$_2$—CH$_2$—CH$_2$—CH$_2$—, —CH$_2$—CH$_2$—CH$_2$—CH$_2$—CH$_2$—, —(CH$_2$)$_2$—O—(CH$_2$)$_2$—O—(CH$_2$)$_2$—, —(CH$_2$)$_2$—O—(CH$_2$)$_2$—O—(CH$_2$)$_2$—O—(CH$_2$)$_2$—, —(CH$_2$)$_2$—O—(CH$_2$)$_2$—O—(CH$_2$)$_2$—O—(CH$_2$)$_2$—O—(CH$_2$)$_2$—, —CH$_2$—CH(—Y)—CH$_2$—, cyclohexane-1,2-diyl, cyclohexane-1,3-diyl or cyclohexane-1,4-diyl, R$_3$ represents (—CH$_2$)$_2$CH—, (—CH$_2$)$_3$—CH$_3$ or (—CH$_2$)$_3$C—CH$_2$—CH$_3$, Y being —H, —CH$_3$, —C$_2$H$_5$, —C$_3$H$_7$ or —C$_4$H$_9$ and m, n, o, p, q and r independently of one another being a whole number from 2 to 18.

It is especially preferred if R is —CH(CH$_3$)—, R$_1$ is —CH(CH$_3$)—COOY, Y is —C$_2$H$_5$ and m, n, o, p, q or r is a whole number from 2 to 4.

Preferred implants have a ratio of biodegradable polymers to oligomer of 1:100 to 1:1 and especially 1:6 to 1:2.

The inventive compositions accordingly contain the above-mentioned biocompatible, biodegradable polymers and oligomers and are used without additional solvents or catalysts.

The inventive compositions may contain biologically active materials. In preferred implants, the coagulate contains at least one biologically active material, for example, from the group comprising hormones, immune modulators, immune suppressive agents, antibiotics, cytostatic agents, diuretics, gastrointestinal drugs, cardiovascular drugs, anti-inflammatory agents, analgesics, local anesthetics and neuropharmacological drugs.

The inventive compositions are flowable in that they can be injected largely without causing pain. They can be subjected to the conventional sterilization methods.

After the inventive compositions, containing the biologically active substance, are placed in the organism, a coagulate is formed under the influence of the body fluid. As this coagulate is decomposed biologically in a process, which make take place over a period lasting formed weeks or months to years depending on the composition of the composition, the biologically active substance is released.

It is therefore preferred that the release of the biologically active substance be controlled by the components of the sterile, injectable composition and their relationship to one another. In this way, it is possible to adapt the rate of release to the pharmacokinetic and pharmacodynamic properties of the active ingredients in the organism.

The object of the present invention furthermore is a method for preparing and implant, wherein, pursuant to the invention, a sterile, injectable composition of a biologically degradable polymer, and a liquid, biologically degradable oligomer is placed in the organism and coagulated under the influence of the body fluid.

The invention is explained by the following examples.

BRIEF DESCRIPTION OF THE DRAWING

The objects, features and advantages of the invention will now be illustrated in more detail with the aid of the following description of the preferred embodiments, with reference to the accompanying figures in which.

EXAMPLES

Figure 1:
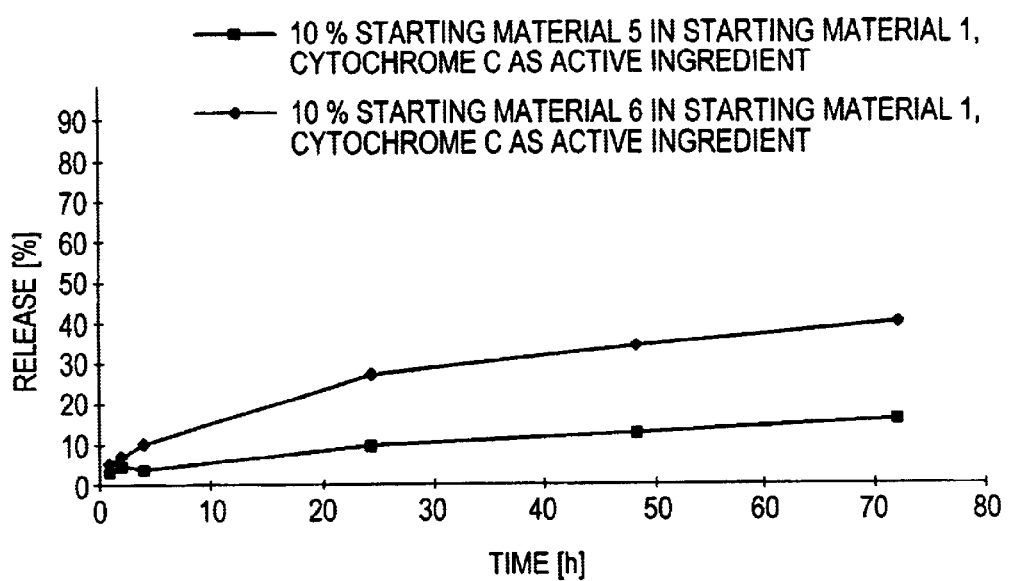
FIG. 1 shows two release profiles of a biologically active ingredient, Cytochrome c, from two examples of the injectable implant composition according to the invention.

Synthesis of Biodegradable, Liquid Oligomers (Examples 1 and 2)

Example 1

Ethyl Ester Oligo-D, L-lactide of L-(−)-Lactic Acid

Under flowing nitrogen, a mixture of 15.0 g (104 mmoles) of D,L-lactide, 12.294 g (104 mmoles) of ethyl of L-(−)-lactate, as well as 2 drops of tin(II) 2-ethyl hexanoate is heated with stirring for 4 hours at 140° C. After the melt is cooled to room temperature, the reaction mixture is dissolved in 40 mL of methylene chloride. This solution is added dropwise to 400 mL of heptane. The product separates out as a viscous oil. The heptane phase of lower density is removed and the solvent residues, remaining in the product, are removed under reduced pressure. Subsequently, the product is dried to constant weight under vacuum. A viscous, colorless oil is obtained. Yield: 16.02 g $M_n$ (VPO): 354 g/mole

Example 2

Ethyl Ester Oligo-L-lactide of L-(−)-Lactic Acid
(Starting Material 2)

Under flowing nitrogen, a mixture of 15.0 g (104 mmoles) of L-lactide, 12.294 g (104 mmoles) of ethyl L-(−)lactate, as well as 2 drops of tin(II) 2-ethyl hexanoate is heated with stirring for 4 hours at 140° C. After the melt is cooled to room temperature, the reaction mixture is dissolved in 40 mL of methylene chloride. This solution is added dropwise to 400 mL of heptane. The product separates out as a viscous oil. The heptane phase of lower density is removed and the solvent residues, remaining in the product, are removed under reduced pressure. Subsequently, the product is dried to constant weight under vacuum. A viscous, colorless oil is obtained. Yield: 19.22 g $M_n$ (VPO): 362 g/mole Synthesis of Biodegradable Polymers (Examples 3 to 9)

Example 3

(Starting Material 3)

Under flowing nitrogen, a mixture of 13.0 g (90.2 mmoles) of D,L-lactide, 0.532 g (4.5 mmoles) of ethyl L-(−)lactate, as well as 2 drops of tin(II) 2-ethyl hexanoate is heated with stirring overnight at 140° C. After the melt is cooled to room temperature, the reaction mixture is dissolved in 40 mL of methylene chloride. This solution is added dropwise to 400 mL of heptane. The product precipitates as a tacky solid. The heptane phase of lower density is subsequently removed. The product is taken up in 40 mL of methylene chloride. After the solvent has been concentrated under reduced pressure, the remaining residues of solvent are removed by drying for several days under vacuum. A glass-like transparent solid is obtained. Yield: 12.450 g $M_n$ (GCP, RI): 4346 g/mole

Example 4

(Starting Material 4)

Under flowing nitrogen, a mixture of 13.0 g (90.2 mmoles) of D,L-lactide, 0.205 g (1.73 mmoles) of ethyl L-(−)lactate, as well as 2 drops of tin(II) 2-ethyl hexanoate is heated with stirring overnight at 140° C. After the melt is cooled to room temperature, the reaction mixture is dissolved in 40 mL of methylene chloride. This solution is added dropwise to 400 mL of heptane. The product precipitates as a tacky solid. The heptane phase of lower density is subsequently removed. The product is taken up in 40 mL of methylene chloride. After the solvent has been concentrated under reduced pressure, the remaining residues of solvent are removed by drying for several days under vacuum. A glass-like transparent solid is obtained. Yield: 9.580 g $M_n$ (GPC, RI): 7790 g/mole

Example 5

(Starting Material 5)

Under flowing nitrogen, a mixture of 13.0 g (90.2 mmoles) of D,L-lactide, 1.835 g (4.5 mmoles) of cholesterol, as well as 2 drops of tin(II) 2-ethyl hexanoate is heated with stirring overnight at 140° C. After the melt is cooled to room temperature, the reaction mixture is dissolved in 40 mL of methylene chloride. This solution is added dropwise to 400 mL of heptane. The product precipitates as a tacky solid. The heptane phase of lower density is subsequently removed. The product is taken up in 40 mL of methylene chloride. After the solvent has been concentrated under reduced pressure, the remaining residues of solvent are removed by drying for several days under vacuum. A glass-like transparent solid is obtained. Yield: 13.905 g $M_n$ (GPC, RI): 4116 g/mole Example 6

(Starting Material 6)

Under flowing nitrogen, a mixture of 13.0 g (90.2 mmoles) of D,L-lactide, 0.918 g (2.25 mmoles) of cholesterol, as well as 2 drops of tin(II) 2-ethyl hexanoate is heated with stirring overnight at 140° C. After the melt is cooled to room temperature, the reaction mixture is dissolved in 40 mL of methylene chloride. This solution is added dropwise to 400 mL of heptane. The product precipitates as a tacky solid. The heptane phase of lower density is subsequently removed. The product is taken up in 40 mL of methylene chloride. After the solvent has been concentrated under reduced pressure, the remaining residues of solvent are removed by drying for several days under vacuum. A glass-like transparent solid is obtained. Yield: 13.528 g $M_n$ (GPC, RI): 8682 g/mole Example 7

(Starting Material 7)

Under flowing nitrogen, a mixture of 13.0 g (90.2 mmoles) of D,L-lactide, 0.343 g (4.5 mmoles) of 1,2-dihydroxypropane, as well as 2 drops of tin(II) 2-ethyl hexanoate is heated with stirring overnight at 140° C. After the melt is cooled to room temperature, the reaction mixture is dissolved in 40 mL of methylene chloride. This solution is added dropwise to 400 mL of heptane. The product precipitates as a tacky solid. The heptane phase of lower density is subsequently removed. The product is taken up in 40 mL of methylene chloride. After the solvent has been concentrated under reduced pressure, the remaining residues of solvent are removed by drying for several days under vacuum. A glass-like transparent solid is obtained. Yield: 12.130 g $M_n$ (GPC, RI): 3794 g/mole Example 8

(Starting Material 8)

Under flowing nitrogen, a mixture of 13.0 g (90.2 mmoles) of D,L-lactide, 0.171 g (2.25 mmoles) of 1,2-dihydroxypropane, as well as 2 drops of tin(II) 2-ethyl hexanoate is heated with stirring for 4 hours at 140° C. After the melt is cooled to room temperature, the reaction mixture is dissolved in 40 mL of methylene chloride. This solution is added dropwise to 400 mL of heptane. The product precipitates as a tacky solid. The heptane phase of lower density is subsequently removed. The product is taken up in 40 mL of methylene chloride. After the solvent has been concentrated under reduced pressure, the remaining residues of solvent are removed by drying for several days under vacuum. A glass-like transparent solid is obtained. Yield: 12.680 g $M_n$ (GPC, RI): 7784 g/mole Example 9

(Starting Material 9)

Under flowing nitrogen, a mixture of 13.0 g (90.2 mmoles) of D,L-lactide, 0.201 g (1.5 mmoles) of 1,1,1-trishydroxymethylpropane, as well as 2 drops of tin(II) 2-ethyl hexanoate is heated with stirring for 4 hours at 140° C. After the melt is cooled to room temperature, the reaction mixture is dissolved in 40 mL of methylene chloride. This solution is added dropwise to 400 mL of heptane. The product precipitates as a tacky solid. The heptane phase of lower density is subsequently removed. The product is taken up in 40 mL of methylene chloride. After the solvent has been concentrated under reduced pressure, the remaining residues of solvent are removed by drying for several days under vacuum. A glass-like transparent solid is obtained. Yield: 12.12 g $M_n$ (GPC, RI): 11053 g/mole Polymer-Oligomer Compositions Example 10

A mixture of 100 mg of poly-D,L-lactide (Example 5, JP 37) and 900 mg oligomeric ester (Example 1, JP 43) is stirred for 5 minutes at 140° C. A viscous, transparent liquid is formed. When this polymer-oligomeric ester is added dropwise to water, a dimensionally stable coagulate is formed.

Release of Biologically Active Materials

Example 11

The viscous, transparent solution of a mixture (of Example 10) of 100 mg of poly-D,L-lactide (starting material 5 or 6) and 900 mg of oligomer (starting material 1) is mixed with 6 mg of cytochrome C, which becomes suspended in the mixture. The suspension is injected into a membrane in a beaker, which contains 500 mL of isotonic sodium chloride solution. The acceptor medium is stirred and the release of cytochrome C from the coagulate, which is formed in situ, is determined after defined time intervals. The release profile is shown in FIG. 1.

Figure 2:
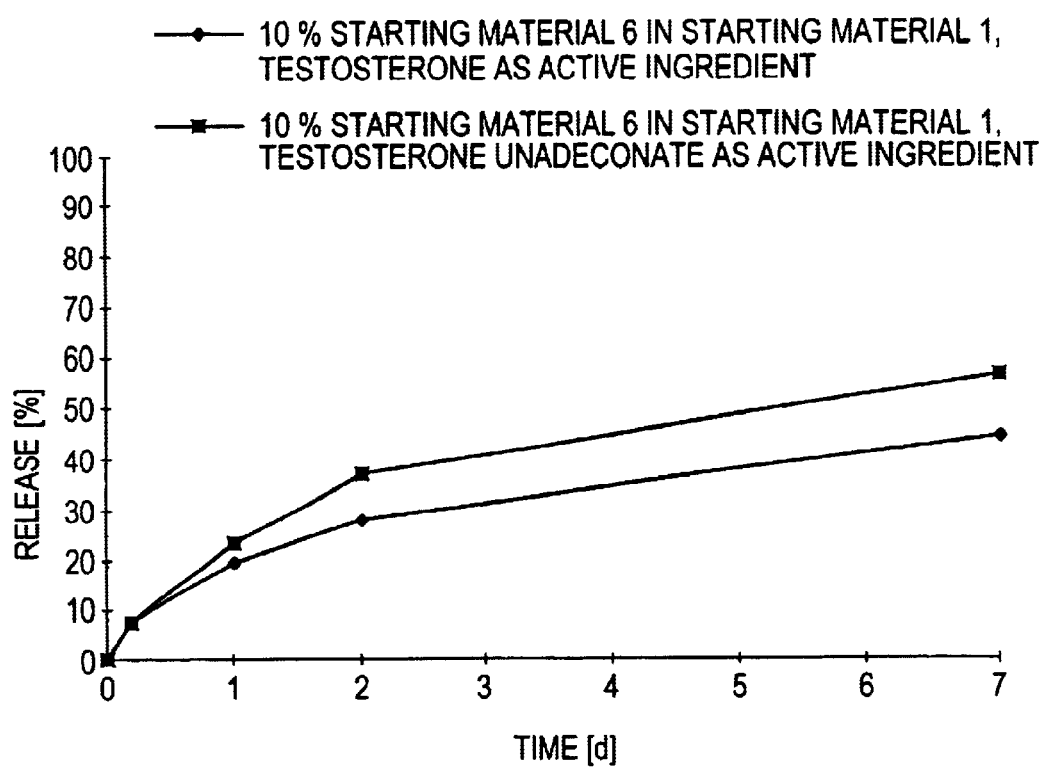
FIG. 2 shows two release profiles of two active ingredients, testosterone and testosterone unadeconate, from another example of the injectable implant composition according to the invention.

The viscous, transparent solution of a mixture (from Example 10) of 100 mg of poly-D,L-lactide (starting material 6) and 900 mg of oligomer (starting material 1) is treated with 6 mg of testosterone or testosterone undecanoate, which becomes suspended in the mixture. The mixture is injected into a membrane in a beaker, which contains 500 mL of isotonic sodium chloride solution. The acceptor medium is stirred and the release of testosterone or testosterone undecanoate C from the coagulate, which is formed in situ, is determined after defined time intervals. The release profile is shown in FIG. 2.

What is claimed is:

1. An injectable liquid oligomer-polymer composition consisting of at least one bioactive substance, at least one solid polymeric hydroxycarboxylic acid easter and at least one liquid oligomeric hydroxycarboxylic acid ester.

2. The injectable liquid oligomer-polymer composition as defined in claim 1, wherein said at least one liquid oligomeric hydroxycarboxylic acid ester is an ester compound of formula I, an ester compound of formula II or an ester compound of formula III:

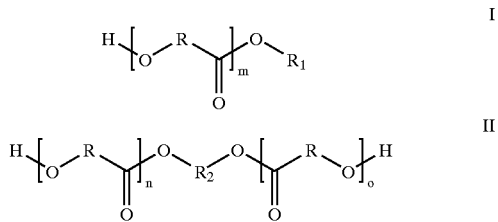

-continued

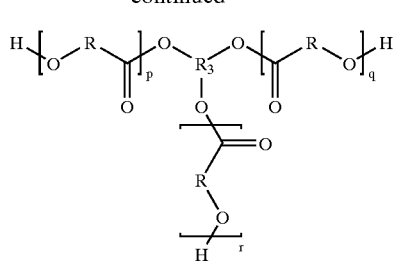

III wherein R for variables m, n, o, p, q and r is identical or different and represents —$CH_2$—, —$CH(CH_3)$—, —$(CH_2)_5$—, —$CH_2$—$CH_2$—O—$CH_2$— or —$CH_2$—$CH_2$—O—$CH_2$—$CH_2$—O—$CH_2$—, or homologues thereof with up to 5 further C atoms in each case; wherein $R_1$ represents —$CH_2$—COOY, —$CH(CH_3)$—COOY, —$CH_2$—$CH_2$—COOY, —$CH_2$—$CH_2$—$CH_2$—COOY, —$CH_2$—$CH_2$—$CH_2$—$CH_2$—COOY, —$CH_2$—$CH_2$—$CH_2$—$CH_2$—$CH_2$—COOY, —$CH_2$—$CH(CH_3)$—Y, —(cyclo—$C_6H_{11}$) or —$CH_2$—$C_6H_5$—; wherein $R_2$ represents —$CH_2$—CH($CH_3$)—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$(CH_2)_2$—O—$(CH_2)_2$—O—$(CH_2)_2$—, —$(CH_2)_2$—O—$(CH_2)_2$—O—$(CH_2)_2$—O—$(CH_2)_2$—, —$(CH_2)_2$—O—$(CH_2)_2$—O—$(CH_2)_2$—O—$(CH_2)_2$—O—$(CH_2)_2$—, —$CH_2$—CH(—Y)—$CH_2$—, cyclohexane-1,2-diyl, cyclohexane-1,3-diyl or cyclohexane-1,4-diyl; wherein $R_3$ represents (—$CH_2$)$_2$CH—, (—$CH_2$)$_3$C—$CH_3$ or (—$CH_2$)$_3$C—$CH_2$—$CH_3$, wherein Y is —H, —$CH_3$, —$C_2H_5$, —$C_3H_7$ or —$C_4H_9$, and m, n, o, p, q and r denote, independently of one another, an integer from 2 to 18.

3. The injectable liquid oligomer-polymer composition as defined in claim 2, wherein said R denotes said —CH($CH_3$)—, said $R_1$ denotes said —CH($CH_3$)—COOY with said Y=said —$C_2H_5$, and said integer is 2, 3 or 4.

4. The injectable liquid oligomer-polymer composition as defined in claim 1, wherein the at least one liquid oligomeric hydroxycarboxylic acid ester is at least one poly(hydroxyester) and/or a copolymer thereof.

5. The injectable liquid oligomer-polymer composition as defined in claim 4, wherein said at least one poly(hydroxyester) is a poly(L-lactide), a poly(D,L-lactide), a poly(glycolide), a poly(caprolactone), a poly(dioxanone), a poly(hydroxybutyric acid), a poly-(hydroxyvaleric acid), a poly(glycosalicylate) and/or a product of ring-opening polymerization of a lactone in the presence of a biocompatible starter molecule.

6. The injectable liquid oligomer-polymer composition as defined in claim 5, wherein said biocompatible starter molecule is an alkyl L-lactide, cholesterol, propane-1,2-diol, triethylene glycol, glycerol or pentaerythritol.

7. The injectable liquid oligomer-polymer composition as defined in claim 1, wherein said at least one solid polymeric hydroxycarboxylic acid ester and said at least one liquid oligomeric hydroxycarboxylic acid ester are present in a ratio of 1:100 to 1:1.

8. The injectable liquid oligomer-polymer composition as defined in claim 7, wherein said ratio is from 1:10 to 1:2.

9. The injectable liquid oligomer-polymer composition as defined in claim 1, wherein said at least one bioactive substance is selected from the group consisting of hormones, immunomodulators, immunosuppressants, antibiotics, cytostatics, diuretics, gastrointestinal agents, cardiovascular agents and neuropharmaceuticals.

10. The injectable liquid oligomer-polymer composition as defined in claim 9, wherein said at least one bioactive substance is present in dissolved or suspended form.

11. An implant obtained by injecting the injectable liquid oligomer-polymer composition as defined in one of claims 1 to 10 into a mammal.

12. A method of preparing an implant for delivering at least one bioactive substance to a mammal, said method comprising the steps of:
a) preparing an injectable liquid oligomer-polymer composition consisting of at least one bioactive substance, at least one solid polymeric hydroxycarboxylic acid ester and at least one liquid oligomeric hydroxycarboxylic acid ester; and
b) injecting said injectable liquid oligomer-polymer composition in said mammal so as to form a coagulum under the influence of body fluid of said mammal.

13. The method as defined in claim 12, wherein said injectable liquid oligomer-polymer composition is defined in one of claims 2 to 10.

14. The coagulum prepared by the method as defined in claim 12.

* * * * *